US011389317B2

(12) United States Patent
Starkey et al.

(10) Patent No.: US 11,389,317 B2
(45) Date of Patent: Jul. 19, 2022

(54) BACK BRACE

(71) Applicant: NEO G LIMITED, Harrogate (GB)

(72) Inventors: Paul Starkey, Harrogate (GB); Okan Ozturkatalay, Istanbul (TR)

(73) Assignee: NEO G LIMITED, Harrogate (GB)

( * ) Notice: Subject to any disclaimer, the term of this patent is extended or adjusted under 35 U.S.C. 154(b) by 73 days.

(21) Appl. No.: 16/461,142

(22) PCT Filed: Nov. 13, 2017

(86) PCT No.: PCT/GB2017/053418
§ 371 (c)(1),
(2) Date: May 15, 2019

(87) PCT Pub. No.: WO2018/091875
PCT Pub. Date: May 24, 2018

(65) Prior Publication Data
US 2019/0274863 A1    Sep. 12, 2019

(30) Foreign Application Priority Data
Nov. 17, 2016   (GB) ..................................... 1619432

(51) Int. Cl.
*A61F 5/02*    (2006.01)

(52) U.S. Cl.
CPC .................................. *A61F 5/028* (2013.01)

(58) Field of Classification Search
CPC .. A61F 5/02; A61F 5/022; A61F 5/024; A61F 5/026; A61F 5/028; A61F 5/00; A61F 5/34; A61F 5/055; A61F 5/05883; A61F 13/14; A61F 5/3707; A61F 5/012; A61F 2007/0009; A42B 3/0473; A47C 7/383
See application file for complete search history.

(56) References Cited

U.S. PATENT DOCUMENTS 6,322,529 B1    11/2001  Chung
2002/0068890 A1*  6/2002  Schwenn .............. A61F 5/0193
                                                          602/19
(Continued)

FOREIGN PATENT DOCUMENTS

WO    2016138215 A1    9/2016

OTHER PUBLICATIONS

"Micrometre" Wikipedia, 2021, pp. 1-4 (Year: 2021).*
(Continued)

*Primary Examiner* — Ophelia A Hawthorne
(74) *Attorney, Agent, or Firm* — Shumaker, Loop & Kendrick, LLP

(57) ABSTRACT

A back brace for providing lumbar stabilisation. The back brace includes a lumbar support having a left support portion and a right support portion. The left and right portions are operable to move from a first position wherein the left and right portions are spaced apart, to a second position wherein the left and right portions are closer together. Each of the left and right lumbar support portions comprise a bar that at least partially delineates at least two apertures in each of the left and right support portions. The brace further comprises a line extending through apertures of the lumbar supports such that actuation of the line moves the left and right portions from the first position to the second position.

10 Claims, 5 Drawing Sheets

(56) References Cited

U.S. PATENT DOCUMENTS

| | | | |
|---|---|---|---|
| 2005/0251074 A1* | 11/2005 | Latham | A61F 5/028 602/19 |
| 2009/0118655 A1* | 5/2009 | Wang | A61F 5/028 602/19 |
| 2010/0217167 A1 | 8/2010 | Ingimundarson et al. | |
| 2011/0295169 A1 | 12/2011 | Hendricks | |
| 2012/0004587 A1 | 1/2012 | Nickel et al. | |

OTHER PUBLICATIONS

International Search Report (ISR) for PCT/GB2017/053418 dated Jan. 23, 2018 (3 pgs.).
Written Opinion for PCT/GB2017/053418 dated Jan. 23, 2018 (6 pgs.).

\* cited by examiner

BACK BRACE

FIELD

The present invention relates to a back brace. More specifically, the present invention relates to back brace for providing lumbar support.

BACKGROUND

Orthotic devices for treating back pain include back braces designed to stabilise the lower back. Such braces may include a support for stabilising the lumbar region. The braces commonly wrap around the torso of a wearer and include a rigid material in the lumbar support to stabilise the lumbar region by providing additional support to the abdomen and spinal column.

It is desirable that back braces allow for variable levels of support to be achieved. Mechanically advantaged systems, such as pulley based lacing systems, can be used in combination with the lumbar support to enable adjustment of the support levels provided by the brace to the lumbar region. However, adjustable back braces containing such systems can be bulky and difficult to conceal. They can also require complex parts and operation of the lacing system can be difficult.

It is an object of aspects of the present invention to address one or more of the abovementioned, or other, problems. In particular, it is an objection of the present invention to provide an adjustable low profile back brace that is easy to operate.

SUMMARY

According to a first aspect of the present invention there is provided a back brace for providing lumbar stabilisation, comprising:
- a lumbar support comprising a left support portion and a right support portion, wherein the left and right portions are operable to move from a first position wherein the left and right portions are spaced apart, to a second position wherein the left and right portions are closer together;
- wherein each of the left and right lumbar support portions comprise a bar that at least partially delineates at least two apertures in each of the left and right support portions;
- the brace further comprising a line extending through apertures of the lumbar supports such that actuation of the line moves the left and right portions from the first position to the second position.

Advantageously, the back brace of the present invention provides an integrated lacing system having a low profile design in combination with targeted compression and improved support.

Suitably, the apertures of the lumbar portions that are at least partially delineated by the bars of the lumbar portions extend from the rear face of the lumbar support through to the front face of the lumbar support. By "rear" it is meant the face of the support that faces toward the torso in use. By "front" it is meant the face of the support that faces away from the torso in use.

The left and right support portions may be considered to comprise an end that is proximal to the spine in use. Suitably the spine-proximal ends of the left and right support portions are opposed. Each support portion may also be considered to comprise an end proximal to the obliques, in use.

Suitably, the apertures are vertically spaced on the support portions. The apertures may be arranged on the support portions toward the spine-proximal ends of the support portions. Preferably, the apertures are arranged along the edge of the spine-proximal end of the support portions. Preferably, the apertures are arranged within the plane of the lumbar support. As such, preferably the apertures do not project outside of the plane of the support, advantageously providing the back brace with a lower profile.

Preferably, the bars of the support portions are rigid bars. By "rigid bars" it is meant that the shape of the bar is not substantially altered in use. The bars may be formed of metal or plastic, preferably metal, such as steel. Preferably, at parts of the bars that delineate the apertures the material of the bar is exposed. Suitably, the exposed parts of the bars have an $R_a$ of 51 µm, preferably 50.6 µm or 50.5 µm, more preferably ≤0.4 µm or ≤0.3 µm. Preferably, the exposed parts of the bars also form part of the edge of the spine-proximal end of the support portions. Advantageously, providing a thin and smooth material at the terminal edge of the support portions improves the ease of adjusting of the lumbar support.

The bars of the support portions may comprise one or more waveforms. As such, preferably, at least part of the bar is not linear. Suitably, the bars comprise a waveform in the parts that delineate the apertures. Said waveform may be curved. Preferably, the edges of the opposed spine-proximal ends of the supports comprise castellation wherein the projections of the castellation are provided by the waveforms of the bars. Preferably, the waveforms of the bars of the left and right portions are offset. Preferably, the bars only delineate a portion of the apertures.

The left and right support portions may each comprise a flexible cover, preferably a textile flexible cover, suitably formed of a knitted fibre. The flexible cover may extend over at least a portion of the bar, preferably the bar is captively held within the cover. Preferably, the cover delineates at least a portion of the apertures of the support portions. Preferably, the apertures are delineated by the cover and bar.

The bars may comprise one or more portions operable to restrict rotation of the waveforms of the bar. Suitably the rotation restriction portions of the bar extend inwardly toward the oblique-proximal end of the support. Suitably, the oblique-extending portions are arranged within the cover of the supports such that out-of-plane movement is restricted by the cover, suitably by the front and rear walls of the cover. Advantageously, the inclusion of oblique-extending portions anchor the waveforms in position such that rotation of the waveforms is restricted.

The support portions may comprise fixing means operable to restrict lateral movement of the waveforms of the bar. Preferably, the fixing means comprises attaching the front and rear walls of the cover adjacent to the waveforms of the bar. The bars may further comprise an additional support portion arranged vertically and spaced inwardly from the waveforms of the bar. Suitably, the waveforms, anchor portions and additional support portion are integrally formed in the bars.

The left and right support portion may each further comprise a rigid support member, suitably a panel. Suitably, the bars and support members of the support portions are adjacent, preferably abutting, more preferably overlapping. Suitably, the cover envelopes the rigid support members and at least a portion of the bars. Preferably, the cover is integrally formed.

Suitably, the line is actuated by pulling the line away from the lumbar support.

According to a second aspect of the present invention there is provided a method for manufacturing a back brace according to the first aspect of the present invention, comprising the steps of:
a) forming at least a first and a second aperture in the cover of the left and/or right support;
b) arranging the bar of the left and/or right support against the cover such that the waveforms are aligned with, and preferably extending outwardly from, the apertures;
c) folding the cover over the bar(s) and optionally a rigid support member;
d) fixing the cover in the folded conformation; and
e) optionally attaching the sides of the cover together adjacent to the waveforms of the bar to restrict lateral movement of the waveforms.

All of the features contained herein may be combined with any of the above aspects in any combination.

For a better understanding of the invention, and to show how embodiments of the same may be carried into effect, reference will now be made, by way of example, to the following figures, in which:

DETAILED DESCRIPTION

FIGS. 1 to 5 show a first embodiment of a back brace 102 according to the present invention. Elongate brace 102 is formed of a series of laterally connected portions. At the centre of brace 102 is lumbar support portion 104, extending either side of portion 104 are left and right oblique support portions 112 and 114, and extending from support portions 112 and 114 are detachable left and right straps 116 and 118, respectively.

Figure 3:
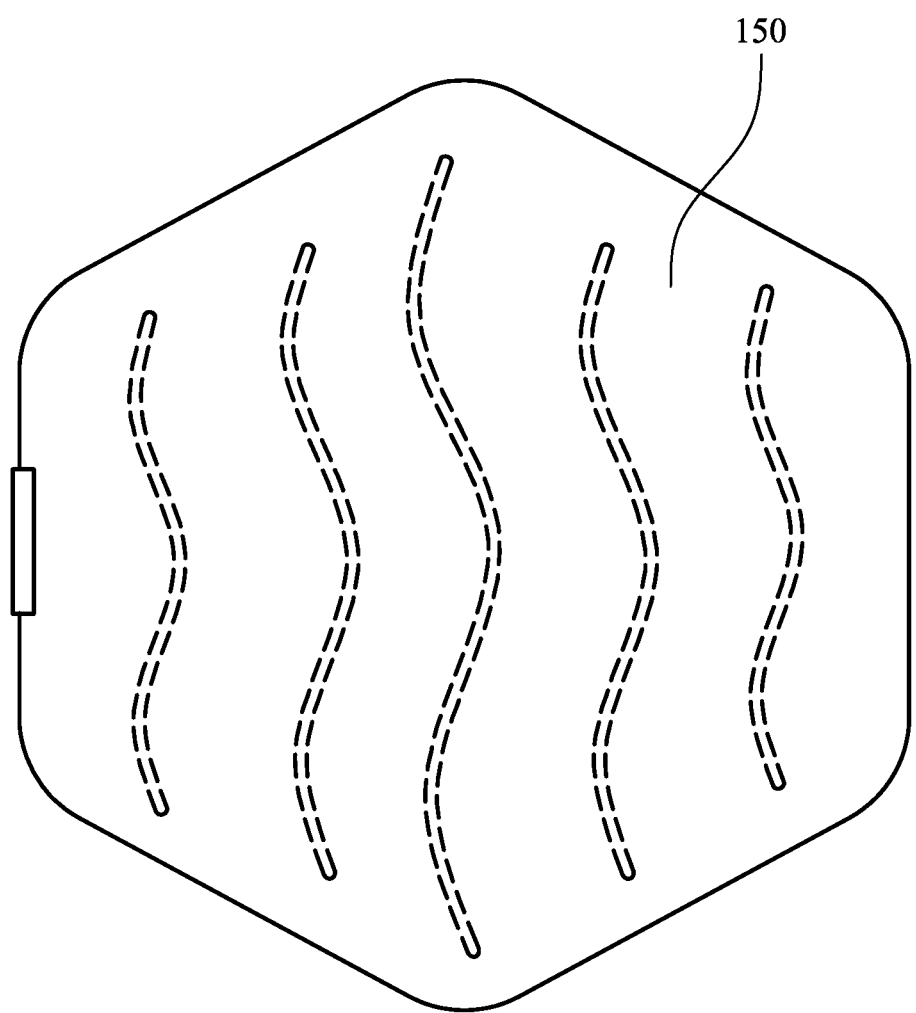
FIG. 3 shows a top view of an optional padded support for use with the back brace of FIG. 1.
Figure 5:
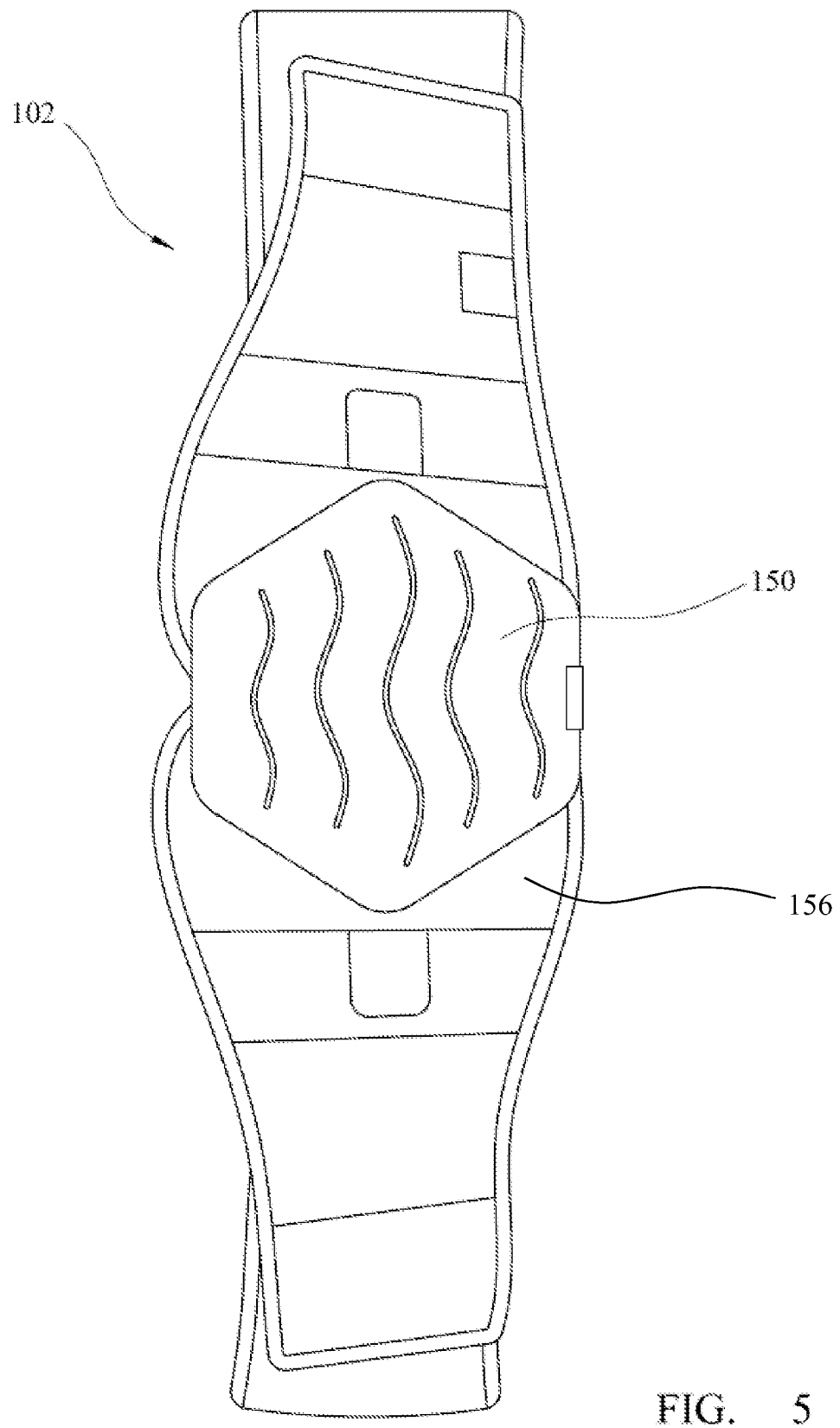
FIG. 5 shows a part rear view of the brace of FIG. 1.

Lumbar support portion 104 is formed of rigid left support 106 and rigid right support 108. Supports 106 and 108 are joined by flexible connector 110. Flexible connector 110 extends from the spine-proximal end of left support 106 to the spine-proximal end of right support 108. Arranged on the rear face of the connector 110 is a patch of hooks for attachment to the loops on the front face of hexagonal padded support 150. As shown in FIGS. 3 and 5, padded support 150 is formed of a series of evenly spaced curved ridges, which are formed of foam covered with a textile material.

Figure 4:
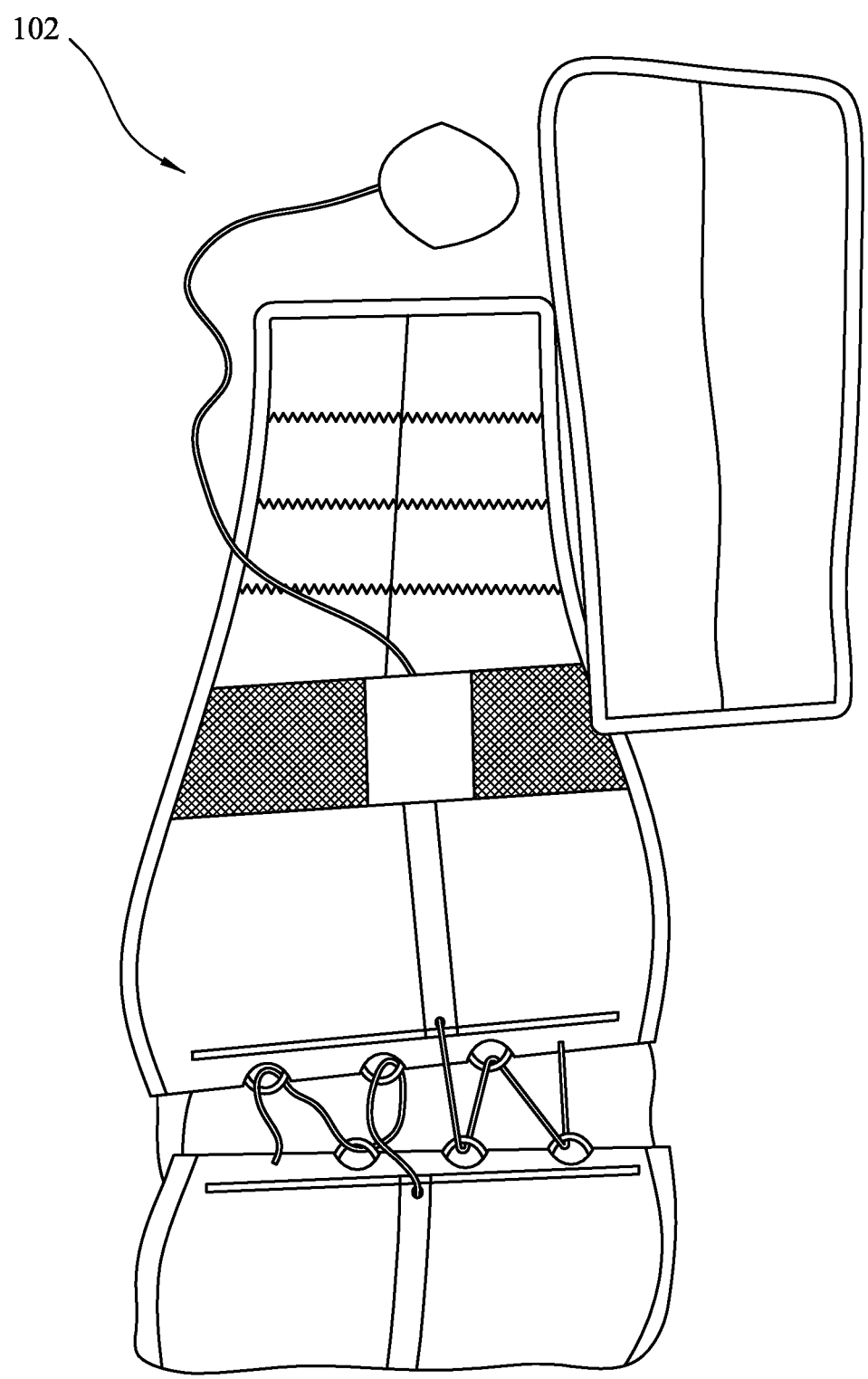
FIG. 4 shows a part top view of the brace of FIG. 1.

Along the oblique-proximal edge of left support 106 is attached left oblique support portion 112. Oblique support 112 is formed of flexible textile portion 122 and rigid portion 120. Flexible portion 122 is joined to left lumbar support 106 along one edge and joined to the rigid portion 120 of oblique support 112 along the laterally opposed edge. Arranged centrally on flexible portion 122 is line guiding member 124. Rigid portion 120 is formed of a rigid panel (not shown) enveloped within a flexible textile cover. Extending across the front face of rigid portion 120 are the loops of a hook and loop attachment system. As shown in FIG. 4, extending vertically across the loops of rigid portion 120 are three spaced lines, each of a different colour. Rectangular flexible strap 116 is formed of textile material and has arranged at one end of the rear face a patch of hooks (not shown) for attachment to the loops of portion 120. Extending across the whole of the front face of strap 116 are loops (not shown) for a hook and loop attachment with hooks arranged at one end of the rear face of the right strap to secure the brace around the waist of a wearer. The coloured lines of the oblique support portions allow for the straps to be quickly and accurately adjusted to a different waist size whilst still allowing for the centre of the lumbar support 104 to be easily arranged about the spine.

Left lumbar support portion 106 is formed of rectangular rigid panel 126, bar 144 and central line guiding member 128. A textile cover envelopes panel 126 and bar 144.

Figure 1:
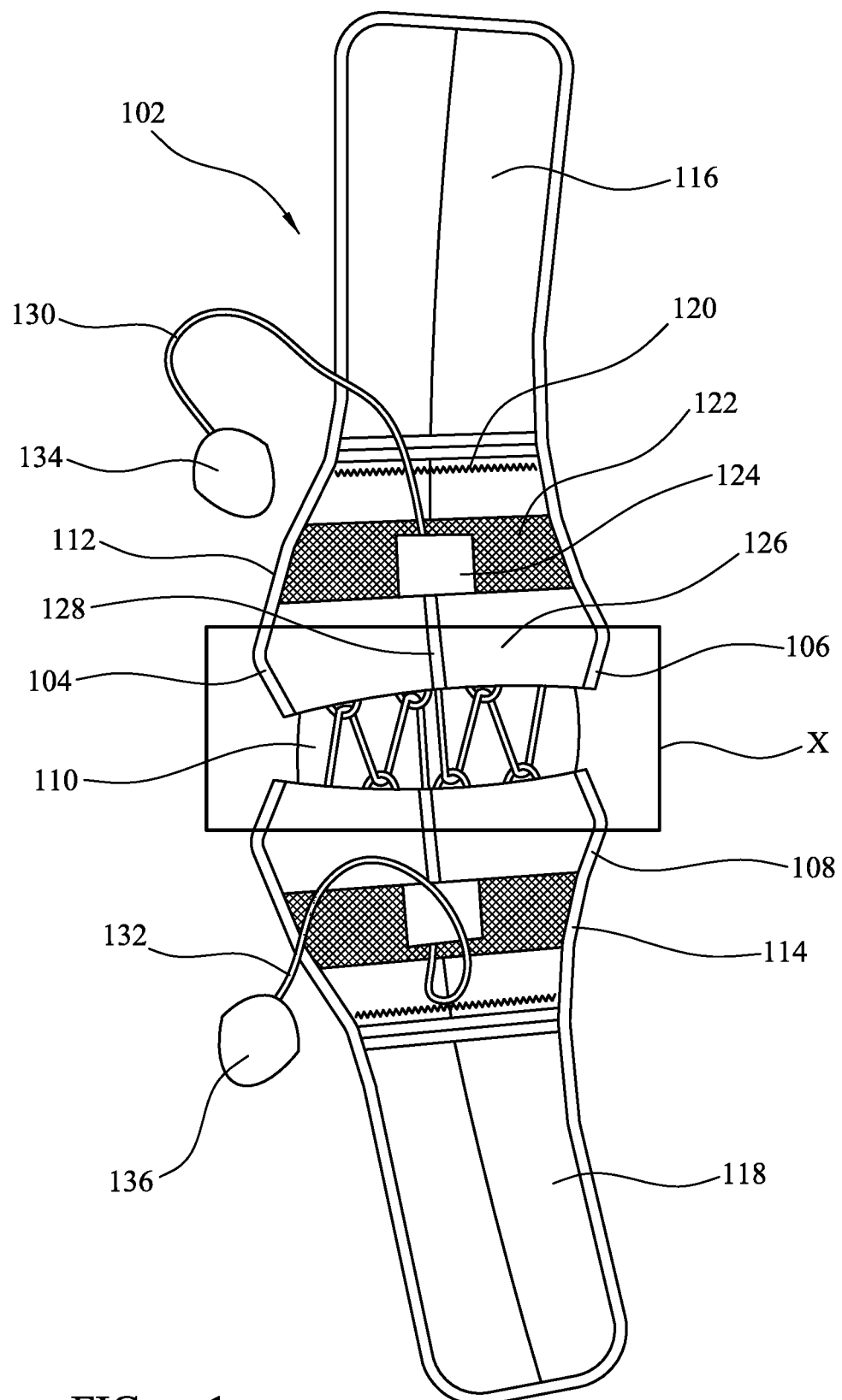
FIG. 1 shows plan view of a first embodiment of a back brace according to the present invention.
Figure 2:
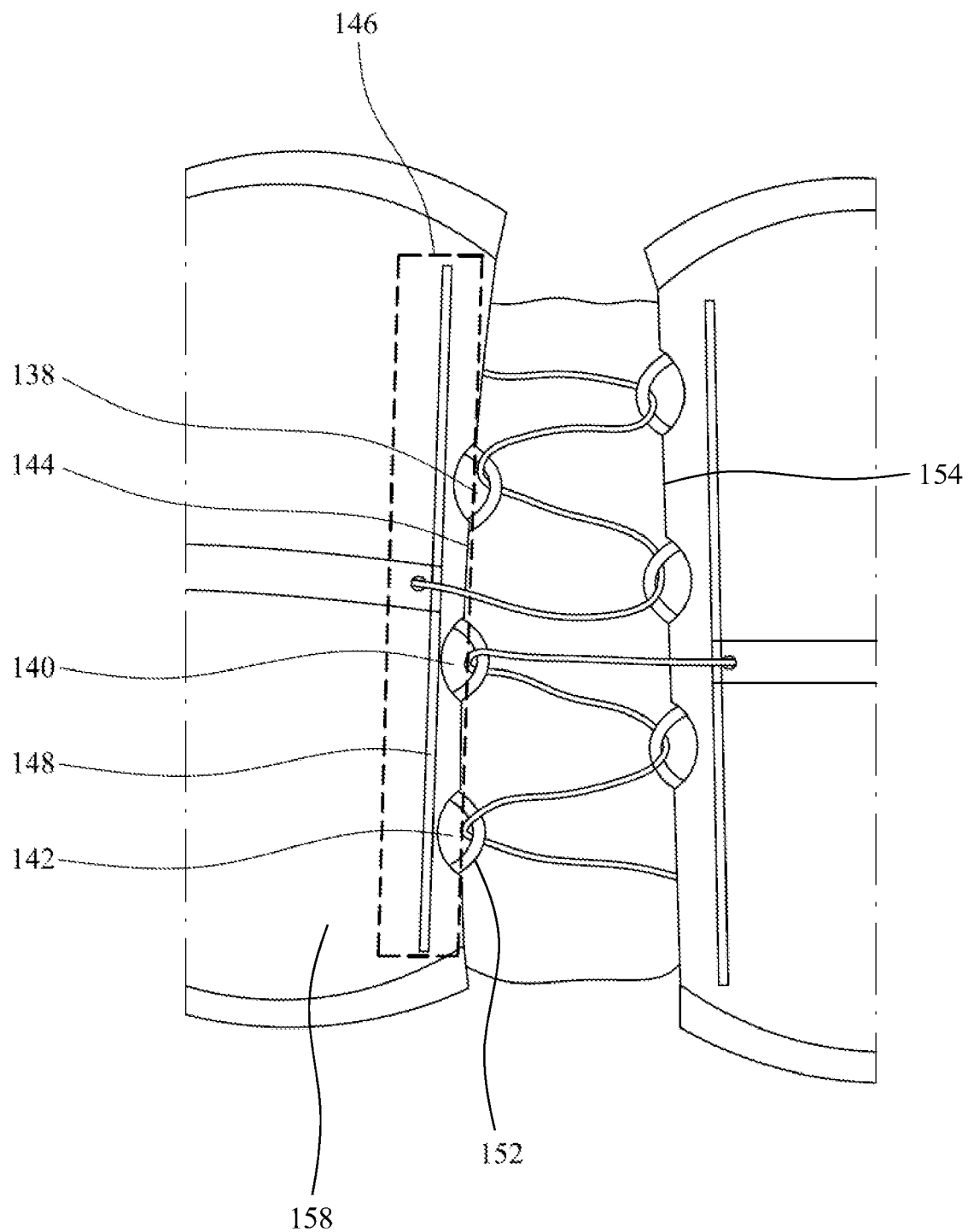
FIG. 2 shows an enlarged view of region X of FIG. 1.

Referring now to FIG. 2, which shows an enlarged view of region X of FIG. 1, it can be seen that three vertically spaced apertures 138, 140 and 142 are arranged on the spine-proximal edge of portion 106. The apertures extend from the rear face of the lumbar support 156 through to the front face of the lumbar support 158. Each aperture is approximately half delineated by exposed portions of smooth bar 144 and half by the flexible cover 154. Bar 144 has curved waveforms 152 extending outwardly from the spine-proximal edge of portion 106 at the points delineating apertures 138, 140 and 142. Apart from the waveforms 152 of bar 144, bar 144 is in the form of a rectangular closed loop. The loop has opposed vertically extending sides, one of which is the waveform-containing side described previously. At each end of waveform-containing side of the loop of bar 144 are sides 146, which extend laterally into the cover from the waveform-containing side of bar 144. Sides 146 serve to anchor the waveform-containing vertical side of bar 144 such that rotation is restricted in use. The ends of sides 146 distal to the waveform-containing side of bar 144 are connected to the other vertical side of the loop of bar 144, said side is linear. Said linear side provides improved stability and support in portion 106.

Apertures 138, 140 and 142 are produced in portion 106 by forming apertures in the cover, arranging bar 144 onto the cover such that the waveforms 152 extend through the apertures and then folding the cover over bar 144, as well as panel 126, and stitching the ends and sides of the cover together such that panel 126 and bar 144 are captively enveloped in the cover. In this process of manufacture the apertures of the cover are folded in half but the waveforms 152 of bar 144 extend through the apertures of the cover to form new apertures 138, 140 and 142. Stitching 148 is then provided within the rectangular loop of bar 144. The stitching extends vertically and parallel to the vertical sides of the loop of bar 144, proximal to the waveform-containing side of bar 144. Stitching 148 attaches the rear and front sides of the cover together such that the waveform-containing side of bar 144 is restricted from lateral movement into the cover.

The right lumbar support 108, right oblique support 114 and right strap 118 of brace 102 are the same as the left side members described above, with the exception that the apertures of the right support portion 108 are vertically offset from the apertures 138, 140 and 142 of left support portion 106. The right strap of brace 102 also has a rounded outer end which further comprises a hook patch on the rear face.

Line 130 is fixedly attached to the spine edge of support 106 at an upper end. Line 130 then extends through the top aperture of the right lumbar support portion 108, through the top aperture 138 of the left lumbar support portion 106 and through the next aperture on the right lumbar support portion 108 before feeding through elongate tunnel line guide means 128 and 124. The free end of line 130 is attached to tab 134. Tab 134 has arranged on the rear face hooks for attachment to the loops on the front face of strap 116. Line 132 is of the same construction of line 130 and is fixedly attached to the spine edge of support 108 at a lower end and extends through aperture 142, the lowest aperture of support 108 and aperture 140 before passing through the guide means of the right side of brace 102.

In use, the wearer arranges the straps 116 and 118 of brace 102 on the oblique portions 112 and 114 of brace 102 at points according to the size of the wear's waist. With straps 116 and 118 attached, the user may then optionally attach padded support 150, before arranging the lumbar support 104 adjacent to the spine of the wearer. The wear then attaches right strap 118 to left strap 116 in order to fix brace 102 around the waist. The level of support provided by brace 102 may then be adjusted by pulling on tabs 134 and 136 to draw left and right lumbar supports 106 and 108 closer together. As supports 106 and 108 are drawn together the level of support provided by brace 102 is increased. Once the desired level of support has been achieved the wearer attaches tabs 134 and 136 to front face of left and right straps 116 and 118, respectively. Brace 102 may be removed by uncoupling the left and right straps 116 and 118.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A back brace for providing lumbar stabilisation, comprising:
   a lumbar support comprising a left lumbar support portion and a right lumbar support portion, wherein the left and right lumbar support portions are operable to move from a first position wherein the left and right lumbar support portions are spaced apart, to a second position wherein the left and right portions are closer together;
   wherein each of the left and right lumbar support portions comprise a bar that defines at least two apertures the respective lumbar support portions;
   wherein the at least two apertures extend from a rear face to a front face of the back brace;
   wherein the bars of the lumbar support portions comprise waveforms in the parts that delineate the apertures;
   and wherein the left and right lumbar support portions each comprise a flexible cover that extends over at least a portion of the respective bar such that the bar is captively enveloped within the flexible cover,
   the brace further comprising a line extending through apertures of the left and right lumbar support portions such that actuation of the line moves the left and right portions from the first position to the second position;
   and wherein the waveforms of the bars are arranged to abut the line during actuation of the line, wherein the portion of the bar that comprises the waveforms that delineate the at least two apertures are integrally formed.

2. The back brace according to claim 1, wherein the left and right lumbar support portion each further comprise a rigid support member.

3. The back brace according to claim 2, wherein the bars and support members of the lumbar support portions are adjacent.

4. The back brace according to claim 2, wherein the flexible cover-envelopes the rigid support members and at least a portion of the bars.

5. The back brace according to claim 1, wherein at parts of the bars that delineate the apertures a material of the bar is exposed.

6. The back brace according to claim 5, wherein the exposed parts of the bars have an $R_a$ of ≤1 μm.

7. The back brace according to claim 1, wherein the apertures are arranged within a plane of the lumbar support.

8. The back brace according to claim 1, wherein edges of opposed spine-proximal ends of the first and second lumbar support portions comprise castellation wherein projections of the castellation are provided by waveforms of the bars.

9. A method for manufacturing a back brace according to claim 1, comprising the steps of:
   a) forming at least a first and a second aperture in a cover of the left and/or right lumbar support portion;
   b) arranging the bar of the left and/or right lumbar support portion against the cover such that waveforms are aligned with, and extending outwardly from, the apertures;
   c) folding the cover over the bar(s) and optionally a rigid support member;
   d) fixing the cover in a folded conformation; and
   optionally attaching the sides of the cover together adjacent to the waveforms of the bar to restrict lateral movement of the waveforms.

10. The back brace according to claim 1, wherein portions of the bar are concealed within a cover of the support and the at least two apertures in each of the left and right support portions comprise exposed portions of the bar extending out of openings formed within the cover of the support to provide an integrated lacing system having a low profile design.

* * * * *